United States Patent [19]

Takayasu et al.

[11] Patent Number: 5,478,568
[45] Date of Patent: Dec. 26, 1995

[54] BUTYROPHENONE TRANSDERMAL COMPOSITIONS

[75] Inventors: Toshiyuki Takayasu; Hideo Saitoh, both of Kasukabe; Eiichi Mafune, Tokyo, all of Japan

[73] Assignees: Saitama Daiichi Pharmaceutical Co., Ltd., Kasukabe; Daiichi Pharmaceutical Co., Ltd., Tokyo, both of Japan

[21] Appl. No.: 230,690

[22] Filed: Apr. 21, 1994

[30] Foreign Application Priority Data

Apr. 28, 1993 [JP] Japan ................................ 5-102958

[51] Int. Cl.$^6$ ............................................ A61F 13/00
[52] U.S. Cl. ...................... 424/449; 424/448; 514/944
[58] Field of Search .................... 429/448, 449; 514/944

[56] References Cited

U.S. PATENT DOCUMENTS 4,409,206 10/1983 Stricker ................................. 424/81
5,118,508 6/1992 Kikuchi ................................ 424/448
5,230,898 7/1993 Horstmann ........................... 424/449

*Primary Examiner*—D. Gabrielle Phelan
*Attorney, Agent, or Firm*—Oblon, Spivak, McClelland, Maier & Neustadt

[57] ABSTRACT

A butyrophenone transdermal composition which comprises the following components (a) to (f):

(a) a water-soluble polymer which is constituted by a monomer containing, partly or wholly, aliphatic carboxylic acid having a polymerizable double bond or a salt of the carboxylic acid, (b) a cross linking agent, (c) a cross linking promoter, (d) water, (e) a butyrophenone drug, and (f) a solvent for the butyrophenone drug (e), as essential components. The pH of the composition is adjusted to fall in the range of 5.5 to 8.0.

With the composition of the invention, the concentration of the active component butyrophenone in blood can be controlled. The composition is capable of exhibiting its primary action, antiemetic action, without causing rash in the skin and with less adverse side effects.

23 Claims, No Drawings

BUTYROPHENONE TRANSDERMAL COMPOSITIONS

BACKGROUND OF THE INVENTION

1. Field of the Invention

The present invention relates to butyrophenone transdermal compositions (hereinafter may be referred to as transdermal compositions) capable of inhibiting vomiting which occurs as an adverse side effect when chemotherapeutic drugs against cancer are administered.

2. Description of the Related Art

Vomiting which occurs as an adverse side effect when chemotherapeutic drugs against cancer are administered is a hindrance in achieving effective cancer treatment. In order to inhibit vomiting caused by the administration of chemotherapeutic drugs against cancer, countermeasures such as massive dose therapy using metoclopramide, combination use of a chemotherapeutic drug and asteroid hormone, and oral administration or injection of butyrophenones or serotonin antagonists have been practiced. However, massive dose therapy of metoclopramide and use of asteroid hormone in combination with other drugs are not very much useful because they involve drawbacks that antiemetic action is weak, and in addition, adverse side effects are caused. On the other hand, serotonin antagonists, which has recently been developed, causes less adverse side effects, but their antiemetic action is still unsatisfactory.

Since vomiting caused by anti-cancer drugs occurs not only during the period of drug administration but also during the suspension period of drugs, the antiemetic effect must last long enough. Conventional antiemetics, however, cannot maintain their effect successfully when they are dosed once a day. Accordingly, patients are forced to take the drugs 3 or even more times a day, or receive intravenous drip in a limited number of well-equipped institutions.

When a patient has vomiting by the use of an anti-cancer drug, antiemetics are hardly administered via oral route due to vomiting, and therefore, their effect cannot be expected. On the other hand, since chemotherapeutic drugs against cancer are generally administered by injection, further injection of antiemetics will bring more suffering to patients, and in addition, such injection involves limitation because it will not be performed in the home treatment.

Butyrophenones have already been used as a psychotropic drug. They have also been used, in the forms of oral or injection preparations, for preventing vomiting which occurs during use of anti-cancer drugs and have exhibited good results. They are, however, accompanied by a shortcoming of causing extrapyramidal side effect. Butyrophenones have a narrow range of concentrations in which the side effect and the primary vomiting-inhibitory action occur. It has therefore been difficult to maintain the drug concentration in blood where only vomiting-inhibitory action is obtained over a long period. Thus, drugs which contain a butyrophenone, which do not cause adverse side effects, and which exhibit lasting effect of vomiting inhibition have been desired. In this regard, patches in the form of films (Japanese Patent Application Laid-open (kokai) No. 232817/1991) and like products have already been developed. Tape articles and plasters of this type can reduce adverse side effects, but still involve drawbacks that severe rash may be induced.

Accordingly, drugs which make the best use of the potent vomiting inhibitory action of butyrophenones over a prolonged period, which are free from adverse side effects, and are dosed easily without causing any pain to patients have still been desired.

Under the above circumstances, the present inventors have carried out extensive studies in search of new transdermal compositions to solve the above-mentioned problems, and have found that when a water-soluble polymer which is obtained from a monomer containing, partly or wholly, aliphatic carboxylic acid having a polymerizable double bond or a salt of the carboxylic acid, a cross linking agent, a cross linking promoter, water, a butyrophenone drug, a solvent for the butyrophenone drug, and optionally a plasticizer, are combined and the pH of the combined material is adjusted to fall in the range of 5.5 to 8.0, an excellent transdermal composition can be obtained which is free from adverse side effects, which exhibits long-lasting vomiting inhibitory effect, and which does not cause rash or the like, leading to completion of the invention.

SUMMARY OF THE INVENTION

According to one aspect of the present invention, there is provided a butyrophenone transdermal composition which comprises the following components (a) to (f):

(a) a water-soluble polymer which is consituted by a monomer containing, partly or wholly, aliphatic carboxylic acid having a polymerizable double bond or a salt of the carboxylic acid, (b) a cross linking agent, (c) a cross linking promoter, (d) water, (e) a butyrophenone drug, and (f) a solvent for the butyrophenone drug (e), as essential components, and in which the pH of said composition is adjusted to fall in the range of 5.5 to 8.0.

According to another aspect of the present invention, there is provided a butyrophenone transdermal composition which comprises the following components (a) to (g):

(a) a water-soluble polymer which is obtained from a monomer containing, partly or wholly, aliphatic carboxylic acid having a polymerizable double bond or a salt of the carboxylic acid, (b) a cross linking agent, (c) a cross linking promoter, (d) water, (e) a butyrophenone drug, (f) a solvent for the butyrophenone drug (e), and (g) a plasticizer, as essential components, and in which the pH of the composition is adjusted to fall in the range of 5.5 to 8.0.

The above and other objects, features and advantages of the present invention will become apparent from the following description.

DETAILED DESCRIPTION OF THE INVENTION AND PREFERRED EMBODIMENTS

The water-soluble polymer (a) in the transdermal composition according to the present invention promotes absorption of the active ingredient, butyrophenone drug (e), by holding a lot of water and enhancing the hydration of the skin. The water-soluble polymer is obtained from a monomer containing, partly or wholly, an aliphatic carboxylic-acid having a polymerizable double bond such as acrylic acid, methacrylic acid, maleic anhydride or the like and a salt of such aliphatic carboxylic acid. Specific examples of such water-soluble polymers include polyacrylic acid, polymethacrylic acid, water-soluble salts of polyacrylic acid, water-soluble salts of polymethacrylic acid and the like, and carboxyvinyl polymers. These water-soluble polymers may be used singly or in combination of two or more. Here, examples of water-soluble salts include water-soluble organic salts which are selected from organic salts typified by alkali metal salts, ammonium salts, and mono-, di- and tri- ethanolamine salts. The most preferable examples of the water-soluble polymer (a) are sodium polyacrylate and potassium polyacrylate.

It is preferred that the water-soluble polymer (a) be incorporated into the transdermal composition of the present invention in amounts from 2 to 15% by weight, more preferably from 2.5 to 10% by weight.

It is known that, when a water-soluble polymer is incorporated in a base composition of patches, the shape of the drug carrying layer cannot generally be maintained due to perspiration during the use of the patches, which is inconvenient (Japanese Patent Application Laid-open (kokai) 3-232817, page 136). In the present invention, this problem was solved based on the finding that an elastic and stable gel can be obtained by adding a cross linking agent (b) and a cross linking promoter (c) to the base composition.

Specific examples of the cross linking agent (b) include inorganic or organic salts such as aluminum hydroxide, aluminum chloride, aluminum sulfate, aluminum acetate and aluminum stearate; double salts such as aluminum alum; aluminates such as sodium aluminate; and water-soluble aluminum compounds such as inorganic aluminum complex salts and organic aluminum chelated compounds.

Among these aluminum compounds, those which are water-soluble but not freely soluble, in other words, those which are sparingly soluble in water dissolve slowly in an aqueous solution of neutral to weakly acidic. Therefore, when they are added to a liquid in a gel state, reaction does not immediately take place, and cross linking proceeds slowly. This feature is favorable because a uniform base can be obtained. On the other hand, cross linking agents which contain divalent metal ions are inclined to form clusters because the reaction instantly proceeds, which makes it difficult to prepare a uniform gel composition, and thus they are not preferable. Accordingly, in the practice of the present invention, aluminum hydroxide is the most preferable from the viewpoint that the reaction proceeds slowly and a uniform base composition is obtainable.

It is preferred that the cross linking agent (b) be incorporated into the transdermal composition of the present invention in amounts from 0.01 to 3.0% by weight, more preferably from 0.05 to 0.5% by weight.

Examples of cross-linking promoter (c) of the present invention include oxyacids such as glycolic acid, lactic acid, malic acid, tartaric acid, gluconic acid and salicylic acid. Of these, tartaric acid is preferred.

The cross-linking promoter (c) is necessary for accelerating the cross linking reaction between the aforementioned ingredients (a) and (b) and for obtaining a stable gel. The ingredient (c) is preferably incorporated in the transdermal composition of the present invention in amounts of 0.2 to 2% by weight, and in particular, from 0.5 to 1.5% by weight.

It is preferred that the water (d) be incorporated into the transdermal composition of the present invention in amounts of 40 to 90% by weight, more preferably 40 to 70% by weight.

Illustrative examples of the butyrophenone drugs (e) which are used in the present invention include the following drugs (1) to (11):

(1) Haloperidol (Chemical name: 4-[4-(4-chlorophenyl)-4-hydroxy-1-piperidinyl]-1-(4-fluorophenyl)-1-butanone), (2) Timiperone (Chemical name: 4-[4-(2,3-dihydro-2-thioxo-1H-benzimidazol-1-yl)-1-piperidinyl]-1-(4-fluorophenyl)-1-butanone), (3) Benperidol (Chemical name: 1-[1-[4-( 4-fluorophenyl)-4-oxobutyl]-4-piperidinyl]-1,3-dihydro- 2H-benzimidazol-2-one), (4) Floropipamide (Chemical name: 1'-[4-( 4-fluorophenyl)-4-oxobutyl]-[1,4'-bipiperidine]-4'-carboxamide), (5) Fluanisone (Chemical name: 1-(4-fluorophenyl)-4-[4-(2-methoxyphenyl)-1-piperazinyl]-1-butanone), (6) Methylperidol (Chemical name: 1-(4-fluorophenyl)-4-[4-hydroxy-4-(4-methylphenyl)-1-piperidinyl]-1-butanone), (7) Trifluperidol (Chemical name: 1-(4-fluorophenyl)-4-[4-hydroxy-4-[3-(trifluoromethyl)phenyl]-1-piperidinyl]-1-butanone), (8) Spiroperidol (Chemical name: 8-[4-(4-fluorophenyl)--oxobutyl]-1-phenyl-1,3,8-triazaspiro[4,5]decan-4-one], (9) Droperidol (Chemical name: 1-[1-[4-( 4-fluorophenyl)-4-oxobutyl]-1,2,3,6-tetrahydro-4-pyridinyl]-1,3-dihydro-2H-benzimidazol-2-one),

(10) Bromoperidol (Chemical name: 4-[4-( 4-buromophenyl)-4'hydroxy-1-piperidinyl]-1-(4-fluorophenyl)-1-butanone), and

(11) Fluoperidol (Chemical name: 1-(4-fluorophenyl)-4-[4-(2-piperidinyl)-1-piperazinyl]-1-butanone).

Of these, timiperone is preferred in view of the discrepancy between the magnitude of extrapyramidal side effect and that of antiemetic effect.

It is preferred that the butyrophenone drug (e) be incorporated into the transdermal composition of the present invention in amounts of 0.1 to 10% by weight, and in particular, 0.3 to 2% by weight.

The solvent (f) functions to accelerate the absorption of the butyrophenone drug (e) and to help the drug dissolve. By the use of the solvent (f), distribution coefficient (skin/base) and diffusion coefficient of the ingredient (e) can be increased.

Specific examples of the solvent (f) include peppermint oil; glycols such as propylene glycol, 1,3-butyrene glycol, 1,4-butyrene glycol, 1,2-butyrene glycol, diethylene glycol, and polyethylene glycol (Macrogol); glycerol; allantoin, dimethylsulfoxide, dimethylacetamide, dimethylformamide, isopropyl myristate, diisopropyl adipate, diethyl sebacate, ethyl laurate, lanolin, mineral oil; pyrrolidone derivatives such as 2-pyrrolidone, 1-methyl-2-pyrrolidone, 1-ethyl-2-pyrrolidone, 1-dodecyl-2-pyrrolidone, 1-methyl-2-pyrrolidone-5-carboxylic acid, and pyrrolidone carboxylic alkyl esters; ethyl lactate, myristyl lactate, linoleic acid, and linolenic acid. Of these solvents, 1-methyl-2-pyrrolidone, propylene glycol, peppermint oil are especially preferred.

It is preferred that the solvent (f) be incorporated into the transdermal composition of the present invention in amounts of 1 to 30% by weight, and in particular, 2 to 20% by weight.

The pH of the transdermal composition of the present invention must be adjusted to fall in the range of 5.5 to 8.0. Preferable pH range is 6.0 to 6.5. In this invention, the term "pH" means the pH which is determined in such a manner that 1 g of a base composition is uniformly dispersed in 10 ml of distilled water, and the glass electrodes of a pH meter is soaked therein for measuring the pH.

It is already known that greater the pH, better the absorption of a drug from the patch to the skin. If the pH exceeds a weakly acidic pH range, a cross linking agent only slowly acts to make the water-soluble polymer (a) to be cross-linked, and therefore, a transdermal composition cannot form a flexible and stable gel. In this case, if an oxyacid, which is a cross-linking promoter, is added for controlling the pH, an excellent preparation which causes less dissolution due to perspiration and which forms a flexible and stable gel can be obtained. Accordingly, in view of the balance between the two functions, namely, drug absorption and cross linking performance, the pH of the present transdermal composition is preferably controlled to fall in the above-described range.

The adjustment of pH can be performed by the use of an oxyacid which is used as ingredient (c), or by the use of carboxyvinyl polymers to be used as ingredient (i) which will be described hereinlater. Alternatively, gel formation may be carried out under the condition of a low pH, and then an alkali agent is added after gel is formed to control the pH in the above range.

In the transdermal compositions of the present invention, a plasticizer (g) may optionally be incorporated in addition to the ingredients (a) to (f). The plasticizer functions to maintain the "flexibility" of the base of the transdermal composition even though water is evaporated to some extent. In other words, if a plasticizer is not contained, the gel of ingredient (a) becomes to be a solid resin-like material when water is evaporated. This may cause loss of "flexibility" of patches and loss of adhesion capability of patches to the skin, but they can be avoided by the additional use of the plasticizer (g). Moreover, the plasticizer (g) functions as a moisturizer to the skin and enhances the hydration of the skin, which is one of factors of enhancing the transdermal absorption of drug.

As an example of the plasticizer (g), glycerol is mentioned. Moreover, the glycols illustrated as examples of the solvent (f) can also be used as a plasticizer. Among them, glycerol is particularly preferred. The proportion of the ingredient (g) is from 5 to 40% by weight, in particular, 10 to 30% by weight based on the total weight of the transdermal composition of the present invention.

Preferable examples of the transdermal composition of the present invention include a composition according to Claim 2, wherein component (f) is pyrrolidone derivative(s) and/or glycol(s), component (g) is glycerol and/or glycol(s), component (a) is a water-soluble salt of polyacrylic acid, component (b) is an aluminum compound, and component (c) is an organic oxyacid; and more particularly, a composition according to Claim 2, wherein component (f) is N-methyl-2-pyrrolidone and/or propylene glycol and/or butyrene glycol, component (g) is glycerol and/or propylene glycol, component (a) is sodium polyacrylate and/or carboxyvinyl polymer and/or polyacrylic acid, component (b) is aluminum hydroxide, component (c) is tartaric acid, and component (e) is timiperone.

In order to enhance the attaching ability (adhesiveness) to the skin, the transdermal composition of the present invention may optionally contain a tackifier as an ingredient (h). The tackifier is preferably a polymer which is insoluble in water, and especially a polymer made of a monomer which contains, partly or wholly, a (meth)acrylic alkyl ester. Specific examples of the polymer include acrylic n-butyl.methacrylic copolymer (Primal N 580NF, by Japan Acrylic Chemical Co., Ltd.), acrylic methyl.acrylic 2-ethylhexyl copolymer (Nikasol TS-6520, by Nippon Carbide Industries Co., Ltd.), polyacrylic acid (JURYMER AC-10LPH, by Nihon Junyaku Co., Ltd.), methacrylic copolymer L (Plastoid L50, by Rohm Pharma GmbH) and aminoalkyl-methacrylate copolymer E (Plastoid E35L, Plastoid E35M, Plastoid E35H, by Rohm Pharma GmbH).

It is preferred that the tackifier (h) be incorporated into the transdermal composition of the present invention in amounts of 0.5 to 20% by weight, and in particular, 0.5 to 5% by weight.

In order to increase the viscosity and shape-retaining ability of the gel for maintaining the functions of patches, the transdermal composition of the present invention may optionally contain a filler as an ingredient (i). Examples of the filler (i) include inorganic powders such as precipitated silicic acid anhydride; cellulose derivatives such as sodium cellulose glycolate (sodium carboxymethylcellulose), methylcellulose, hydroxyethylcellulose, hydroxypropylcellulose and hydroxypropylmethylcellulose; synthesized polymers such as polyvinylalcohol and polyvinylpyrrolidone; gelatin, gums, and starch. In addition, the carboxyvinyl polymers which were mentioned as a water-soluble polymer (a) can also be used as a filler. Of the above materials, precipitated silicic acid anhydride can serve as a filler and as a capacity increasing agent, too. Moreover, since carboxyvinyl polymer gel is acidic in the state of an aqueous solution, when it is incorporated into a base composition, it can increase the attaching performance (adhesiveness) of the transdermal composition to the skin, and is also useful as a buffering agent (pH modifier) of the property of the base composition in terms of the liquid property.

It is preferred that the filler (i) be incorporated into the transdermal composition of the present invention in amounts of 0.2 to 5% by weight, and in particular, 0.5 to 2% by weight.

The transdermal composition of the present invention may optionally contain, as ingredient (j), a surfactant which is ordinarily used as a topical agent or a cosmetic ingredient. Especially preferable examples of the surfactant include polyoxyethylene hydrogenated castor oil and sorbitan fatty acid ester.

It is preferred that the surfactant (j) be incorporated into the transdermal composition of the present invention in amounts of 0.1 to 2.0% by weight, and in particular, 0.2 to 0.7% by weight.

The transdermal composition of the present invention may be prepared by blending the essential ingredients (a) to (f) and optional ingredients (g) and (h) to (j) in any order of addition. However, the following method is preferable in view of a uniform kneading without producing undissolved lumps and time saving before a uniform base is obtained.

That is, a filler (i) and a water-soluble polymer constituted by a monomer containing, partly or wholly, aliphatic carboxylic acid having a polymerizable double bond or a salt of the carboxylic acid (a) are dispersed in a portion of a plasticizer (g), and the obtained dispersion is added to purified water (d) followed by kneading. By this procedure, a gel-like liquid is obtained, which will be called liquid A. Next, a butyrophenone drug (e) is added to a mixture of the remainder of a plasticizer (g), a solvent (f) and a surfactant (i) for dispersion. This dispersion will be called liquid B. Liquid B is gradually added to liquid A as prepared above, or alternatively, liquid A is gradually added to liquid B, and the resulting mixture is subjected to kneading. A cross linking agent (b) and a cross linking promoter (c) are further added to the kneaded material and uniformly mixed, to which a tackifier (h) is added and the pH is adjusted to 5.5 to 8.0.

The thus-obtained transdermal composition of the present invention is preferably spread on a backing and used as a patch. Preferable backing is a nonwoven fabric. Alternatively, flannel cloth and plastic films can be used. If desired, plastic films may be used for wrapping in order to prevent drying and to maintain the stability and uniform quality of the patch.

Examples of other possible forms of transdermal composition of the present invention include poultices, plasters, ointments, tapes and films.

Since the transdermal compositions of the present invention possess an enhanced ability of absorbing the active ingredient, butyrophenone drugs, the compositions exhibit excellent antiemetic action, and onset of the antiemetic action is immediate. That is, immediate effect can be obtained. Moreover, when the compositions are used in the form of a patch as spread on a backing of the patch, the following advantages are obtained: Interindividual difference is reduced compared to the cases of oral or injection administrations of butyrophenone drugs; controlling of the drug concentration in blood is easy because a patch can be easily removed off from the skin; effective blood concentration can be continued for an arbitrary period of time; and adverse side effects are effectively controlled. Furthermore, users are free from pain which they suffer when the drugs are administered by injection. In addition, with the transdermal compositions according to the present invention, hydration of the skin is elevated because a large quantity of water can be held in a base, which improves the absorption rate of the drugs while reducing chances of causing rash in the skin.

EXAMPLES

The present invention will further be described in more detail by way of examples, which however should not be construed as limiting the invention thereto.

EXAMPLE 1

| Patch (Formulation) | (parts) |
|---|---|
| (1) Precipitated silisic anhydride | 2 |
| (2) Sodium polyacrylate | 5 |
| (3) Carboxyvinyl polymer | 1 |
| (4) Sodium cellulose glycolate | 1 |
| (5) Glycerol | 30 |
| (6) Purified water | 55.95 |
| (7) Timiperone | 0.5 |
| (8) Peppermint oil | 1 |
| (9) Polyoxyethylene hydrogenated castor oil | 0.3 |
| (10) Sorbitan fatty acid ester | 0.3 |
| (11) Aluminum hydroxide | 0.07 |
| (12) Tartaric acid | 0.9 |

(Process)

A. Ingredients (1) through (4) were dispersed in 15 parts of ingredient (5). The resulted dispersion was added to ingredient (6) and kneaded.

B. Ingredient (7) was dispersed in a mixture of the remainder of ingredient (5) and ingredients (8) through (10).

C. The dispersion obtained in Step B was added to the kneaded material obtained in Step A. To the resulted mixture, ingredients (11) and (12) were further added and uniformly mixed to obtain a transdermal composition having a pH of 6.26. The obtained composition was spread onto a nonwoven fabric, and the applied fabric was cut into a suitable size, thereby obtaining a patch of the present invention.

EXAMPLE 2

| Patch (Formulation) | (parts) |
|---|---|
| (1) Sodium polyacrylate | 6 |
| (2) Carboxyvinyl polymer | 1 |
| (3) Polyacrylic acid | 1 |
| (4) Concentrated glycerol | 30 |
| (5) Propylene glycol | 10 |
| (6) 1-Methyl-2-pyrrolidone | 2 |
| (7) Purified water | 48.5 |
| (8) Aluminum hydroxide | 0.2 |
| (9) Tartaric acid | 0.8 |
| (10) Timiperone | 0.5 |

(Process)

A. Ingredient (9) was added to ingredient (7) and dissolved. Ingredients (2) and (3) were added to the resulted solution and dispersed therein.

B. Ingredients (4) and (5) were mixed. To the obtained mixture, ingredients (1) and (8) were added for dispersion. The dispersion was added to A and kneaded.

C. Ingredient (10) was added to ingredient (6) and dissolved. The resulted solution was added to B and uniformly kneaded to obtain a transdermal composition having a pH of 6.2. The obtained composition was spread onto a nonwoven fabric, and the applied fabric was cut into a suitable size, thereby obtaining a patch of the present invention.

Comparative Example 1

| Patch (Formulation) | (parts) |
|---|---|
| (1) Precipitated silisic anhydride | 2 |
| (2) Sodium polyacrylate | 5 |
| (3) Carboxyvinyl polymer | 1 |
| (4) Sodium cellulose glycolate | 3 |
| (5) Glycerol | 30 |
| (6) Purified water | 55.9 |
| (7) Timiperone | 0.5 |
| (8) Peppermint oil | 1 |
| (9) Polyoxyethylene hydrogenated castor oil | 0.3 |
| (10) Sorbitan fatty acid ester | 0.3 |
| (11) Aluminum hydroxide | 0.05 |
| (12) Tartaric acid | 0.9 |
| (13) Phosphoric acid | Suitable amount |

(Process)

A. Ingredients (1) through (4) were dispersed in 15 parts of ingredient (5). The resulted dispersion was added to ingredient (6) and kneaded.

B. Ingredient (7) was dispersed in a mixture of the remainder of ingredient (5) and ingredients (8) through (10).

C. The dispersion obtained in Step B was added to the kneaded material obtained in Step A. To the resulted mixture, ingredients (11) to (13) were further added and uniformly mixed to obtain a transdermal composition having a pH of 5.33. The obtained composition was spread onto a nonwoven fabric, and the applied fabric was cut into a suitable size, thereby obtaining a patch of the present invention.

Comparative Example 2

| Patch (Formulation) | (parts) |
| --- | --- |
| (1) Precipitated silisic anhydride | 2 |
| (2) Sodium polyacrylate | 5 |
| (3) Carboxyvinyl polymer | 1 |
| (4) Sodium cellulose glycolate | 1 |
| (5) Glycerol | 30 |
| (6) Purified water | 52.95 |
| (7) Timiperone | 0.5 |
| (8) Peppermint oil | 1 |
| (9) Polyoxyethylene hydrogenated castor oil | 0.3 |
| (10) Sorbitan fatty acid ester | 0.3 |
| (11) Aluminum hydroxide | 0.05 |
| (12) Tartaric acid | 0.9 |
| (13) Lactic acid | Suitable amount |

(Process)

A. Ingredients (1) through (4) were dispersed in 15 parts of ingredient (5). The resulted dispersion was added to ingredient (6) and kneaded.

B. Ingredient (7) was dispersed in a mixture of the remainder of ingredient (5) and ingredients (8) through (10).

C. The dispersion obtained in Step B was added to the kneaded material obtained in Step A. To the resulted mixture, ingredients (11) to (13) were further added and uniformly mixed to obtain a transdermal composition having a pH of 4.63. The obtained composition was spread onto a nonwoven fabric, and the applied fabric is cut into a suitable size, thereby obtaining a patch of the present invention.

Comparative Example 3

| Plaster (1) | |
| --- | --- |
| (1) Ethanol | 38 |
| (2) Polyvinylacetal diethylacetate (AEA, product of Sankyo) | 1 |
| (3) Polyvinylpyrrolidone K-90 (Japanese Pharmacopoeia) | 1 |
| (4) Timiperone | 0.17 |
| (5) Sodium salicilate | 0.056 |

(Process)

A. Ingredients (2) and (3) were added to ingredient (1) and dissolved. Ingredients (4) and (5) were added to the resulted solution, and dissolved by stirring.

B. 8 parts of the resulted liquid in Step A were cast into a Teflon-coated Petri dish, and ethanol was allowed to evaporate to obtain a film plaster.

Comparative Example 4

| Plaster (2) | |
| --- | --- |
| (1) Primal N-580NF | 25 |
| (2) Propylene glycol | 6 |
| (3) Polyvinylpyrrolidone | 1 |
| (4) 1-Methyl-2-pyrrolidone | 6 |
| (5) Timiperone | 0.74 |

(Process)

A. Ingredients (2) and (3) were added to ingredient (1) and dissolved.

B. Ingredient (5) was added to ingredient (4) and dissolved. The resulted solution was added to A and mixed.

C. B was spread onto a silicone-treated release paper.

D. C was dried for more than 3 hours at 50° C. and polyolefin film was attached to the surface of the base, followed by cutting into a suitable size to obtain a plaster.

Test Example 1

Anti-apomorphine action of the composition of the present invention (Example 1) was compared to the action of Comparative Examples 1 to 3.

On the day before the test, abdomen hair of rats was shaved by the use of an electric clipper and an electric shaver under etherization. 8 hours prior to the administration of apomorphine, each sample was attached to the abdomen of each rat. The samples (2×3.5 cm) of Example 1 and Comparative Examples 1 and 2 were attached to the abdomen skin which was shaved on the previous day, and covered with aluminum foil (3×4 cm). The covered area was entirely wrapped in an adhesive tape (Nichiban Co., Ltd.) The plaster of Comparative Example 3 was tested in such a manner that it was attached to an adhesive tape, and then attached to the abdomen skin of the rat. The applied part was also occulusively dressed by the use of an adhesive tape.

When 7.5 hours had elapsed after samples were attached, each rat was transferred to an individual plastic cage with a metallic top cover. Thirty minutes later, apomorphine (1.25 mg/kg) was injected into the tail vein of each rat. Twenty minutes thereafter, rats were observed with respect to behaviors of sniffing, licking and biting, which are stereotyped behaviors caused by apomorphine. Observation lasted for 1 minute. When the sample inhibited all the stereotyped behaviors, it was determined to have anti-apomorphine action.

Among the total 10 cases, the sample of Example t inhibited the stereotyped behaviors caused by apomorphine of sniffing in 10 cases, licking in 8 cases, and biting in 6 cases. The overall inhibition rate against the action of apomorphine was 50%.

In the samples of Comparative Examples, as the pH of the composition lowered, the inhibition rate went down, which indicates decreased antiemetic effect. In the test using a plaster of Comparative Example 3 on 9 rats, sniffing was inhibited in 2 rats, licking was inhibited in 5 rats and biting was inhibited in 5 rats. The overall inhibition rate against the action of apomorphine was 11% (1/9). The results clearly show that the sample of the present invention is superior to the film-type plaster with respect to the anti-apomorphine action.

TABLE 1

Effects of compositions on stereotyped behaviors induced by by apomorphine

| Compositions | pH | Number of cases | Stereotyped behaviors | | | Overall inhibition (a) + (b) + (c) | Inhibition rate (%) |
| --- | --- | --- | --- | --- | --- | --- | --- |
| | | | sniffing (a) | licking (b) | biting (c) | | |
| Example 1 | 6.26 | 10 | 10 | 8 | 6 | 5 | 50 |
| Comparative Example 1 | 5.33 | 10 | 6 | 3 | 5 | 2 | 20 |
| Comparative Example 2 | 4.63 | 10 | 0 | 1 | 2 | 0 | 0 |
| Comparative Example 3 | — | 9 | 2 | 5 | 5 | 1 | 11 |

Test Example 2

A sample obtained in Example 2 and a sample obtained in Comparative Example 4 were compared with regard to the transdermal absorption rate using rats.

On the day before the test, abdomen hair of rats was shaved by the use of an electric clipper and an electric shaver under etherization. A sample obtained in Example 2 of the present invention and a plaster (2) obtained in Comparative Example 4 were each cut into pieces having a size of 2×3.5 cm. They were to the bare skin of the abdomen, and immediately covered with aluminum foil (3×4 cm). The trunk of the rat was bound round in an adhesive tape (Nichiban Co., Ltd.) so that the covered area was entirely wrapped. The period of use of the samples was 8 hours. At the elapses of 4 hours and 8 hours after samples were attached, blood was collected from the jugular vein and from the abdominal vein, respectively. The blood was centrifugally separated (3000 rpm, 10 min.) and 0.5 ml of plasma was obtained. Timiperone in the plasma was extracted by the use of an organic solvent. The amount of plasma timiperone remained unchanged was determined by liquid chromatography using spiroperidol as internal standard.

The concentrations of the unchanged plasma timiperone were 22.9 and 14.3 ng/ml after 4 hours and 8 hours of attachment of the sample of Example 2, respectively. By contrast, the concentrations were 4.7 and 3.8 ng/ml after 4 hours and 8 hours of attachment of the plaster of Comparative Example 4, respectively. The sample of Example 2 exhibited a blood concentration which was 5 times higher than the use of the plaster of Comparative Example 4, demonstrating excellent transdermal action of the present invention.

TABLE 2

Transdermal absorption of timiperone

| Compositions | pH Dose | Concentrations of unchanged plasma timiperone (ng/ml) | |
| --- | --- | --- | --- |
| | | 4 hours after application | 8 hours after application |
| Example 2 | 6.2  2.5 mg/rat | 22.9 ± 9.4 | 14.3 ± 2.1 |
| Comparative Example 4 | 6.9  2.5 mg/rat | 4.7 ± 1.7 | 3.8 ± 0.7 |

What is claimed is:

1. A butyrophenone transdermal composition which comprises the following components (a) to (f):
   (a) a water-soluble polymer which is constituted by a monomer containing, partly or wholly, aliphatic carboxylic acid having a polymerizable double bond or a salt or the carboxylic acid,
   (b) a cross linking agent,
   (c) a cross linking promoter,
   (d) water,
   (e) a butyrophenone drug, and
   (f) a solvent for the butyrophenone drug (e), as essential components, and in which the pH of said composition is adjusted to fall in the range of 5.5 to 8.0 and wherein said cross linking agent and cross linking promoter are present in elastic and stable gel producing amounts.

2. A butyrophenone transdermal composition which comprises the following components (a) to (g):
   (a) a water-soluble polymer which is constituted by a monomer containing, partly or wholly, aliphatic carboxylic acid having a polymerizable double bond or a salt of the carboxylic acid,
   (b) a cross linking agent,
   (c) a cross linking promoter,
   (d) water,
   (e) a butyrophenone drug,
   (f) a solvent for the butyrophenone drug (e), and
   (g) a plasticizer,
as essential components, and in which the pH of the composition is adjusted to fall in the range of 5.5 to 8.0 and wherein said cross linking agent and cross linking promoter are present in elastic and stable gel producing amounts.

3. The composition according to claim 1, further comprising: (h) a tackifier.

4. The composition according to claim 2, further comprising: (h) a tackifier.

5. The composition according to claim 1, wherein said cross linking agent (b) is an aluminum compound.

6. The composition according to claim 2, wherein said cross linking agent (b) is an aluminum compound.

7. The composition according to claim 3, wherein said cross linking agent (b) is an aluminum compound.

8. The composition according to claim 1, wherein said cross linking promoter (c) is a hydroxy acid.

9. The composition according to claim 2, wherein said cross linking promoter (c) is a hydroxy acid.

10. The composition according to claim 3, wherein said cross linking promoter (c) is a hydroxy acid.

11. The composition according to claim 4, wherein said cross linking promoter (c) is a hydroxy acid.

12. The composition according to claim 2, wherein said plasticizer (g) is glycerol, propylene glycol or a butyrene glycol.

13. The composition according to claim 2, wherein component (f) is a pyrrolidone derivative and/or a glycol, component (g) is glycerol and/or a glycol, component (a) is a water-soluble salt of polyacrylic acid, component (b) is an aluminum compound, and component (c) is an organic hydroxy acid.

14. The composition according to claim 2, wherein component (f) is N-methyl-2-pyrrolidone and/or propylene glycol and/or butyrene glycol, component (g) is glycerol and/or propylene glycol, component (a) is a sodium polyacrylate and/or carboxyvinyl polymer and/or polyacrylic acid, component (b) is aluminum hydroxide, component (c) is tartaric acid, and component (e) is timiperone.

15. A patch which comprises a butyrophenone transdermal composition as defined in claim 1 and a backing therefor.

16. A patch which comprises a butyrophenone transdermal composition as defined in claim 2 and a backing therefor.

17. A patch which comprises a butyrophenone transdermal composition as defined in claim 3 and a backing therefor.

18. A patch which comprises a butyrophenone transdermal composition as defined in claim 4 and a backing therefor.

19. A patch which comprises a butyrophenone transdermal composition as defined in claim 5 and a backing therefor.

20. A patch which comprises a butyrophenone transdermal composition as defined in claim 6 and a backing therefor.

21. A patch which comprises a butyrophenone transdermal composition as defined in claim 8 and a backing therefor.

22. A patch which comprises a butyrophenone transdermal composition as defined in claim 9 and a backing therefor.

23. A patch which comprises a butyrophenone transdermal composition as defined in claim 12 and a backing therefor.

\* \* \* \* \*